United States Patent [19]

Penn

[11] 4,124,029
[45] Nov. 7, 1978

[54] HEART PACEMAKERS
[75] Inventor: Alan W. Penn, Reading, England
[73] Assignee: United Kingdom Atomic Energy Authority, London, England
[21] Appl. No.: 843,264
[22] Filed: Oct. 18, 1977
[30] Foreign Application Priority Data
Oct. 20, 1976 [GB] United Kingdom .............. 43577/76
[51] Int. Cl.² ............................................. A61N 1/36
[52] U.S. Cl. ................................................ 128/419 P
[58] Field of Search ........ 128/419 P, 419 PG, 419 PS

[56] References Cited
U.S. PATENT DOCUMENTS

| 3,122,597 | 2/1964 | Lenieux | 174/84 R |
|---|---|---|---|
| 3,822,707 | 7/1974 | Adducci et al. | 128/419 P |
| 3,866,616 | 2/1975 | Purdy et al. | 128/419 PS |
| 3,906,959 | 9/1975 | Cannon | 128/419 P |
| 3,986,514 | 10/1976 | Cannon | 128/419 PS |

FOREIGN PATENT DOCUMENTS 961,770  6/1964  United Kingdom .............. 174/152 R Primary Examiner—William E. Kamm
Attorney, Agent, or Firm—Larson, Taylor and Hinds

[57] ABSTRACT

A heart pacemaker device including a pulser unit, an output connector and an output lead connecting the pulser unit to the output connector the whole being encapsulated in a biologically inert material, wherein the output connector incorporates a shroud portion covering the junction between the output lead and the output connector and there is provided an annular deformable sealing member in intimate contact with the shroud portion so as to prevent a body fluid migrating along the surface of the shroud portion of the output connector from gaining access to the junction between the output lead and the output connector.

9 Claims, 3 Drawing Figures

HEART PACEMAKERS

The present invention relates to heart pacemakers, that is to say, devices which produce a regular train of small electrical pulses which when applied to a failing heart stimulates it into functioning properly.

It is usual practice for heart pacemakers to be implanted into the bodies of users where they remain for their working life of some years. Many body fluids are corrosive or are electrolytes, and it is necessary therefore to encapsulate the heart pacemakers in some inert, biologically acceptable material so as to isolate the heart pacemaker module from its environment.

Some erstwhile suitable encapsulants, such as epoxy resins, undergo dimensional changes as a result of interactions with body fluids, causing the bond between the encapsulant and the heart pacemaker module to be broken so allowing the ingress of body fluids to the heart pacemaker module, with consequent corrosion leading to early failure of the device.

A particular problem occurs in heart pacemakers which incorporate an output connection to which a separate catheter is attached to electrically connect the pacemaker to the user's heart, in that body fluids can find their way along to the surface of the output socket and corrode the junction between the output socket and an output lead from a pulser unit incorporated into the pacemaker module.

According to the present invention there is provided a heart pacemaker device including a pulser unit, an output connector and an output lead connecting the pulser unit to the output connector the whole being encapsulated in a biologically inert material, wherein the output connector incorporates an axially extending shroud portion covering the junction betwen the output lead and the output connector and there is provided an annular deformable sealing member in intimate contact with the shroud portion so as to prevent a body fluid migrating along the surface of the shroud portion of the output connector from gaining access to the junction between the output lead and the output connector.

Preferably the deformable sealing member is elastic and the encapsulating material is such that it contracts on curing, so that initially the sealing member is in a state of compression. A suitable encapsulant is epoxy resin.

In a preferred embodiment the sealing member encloses the free end of the shroud portion although it can be attached to either the inner or the outer surface of the shroud portion.

The invention will now be described, by way of example, with reference to the accompanying drawings in which.

Figure 1:
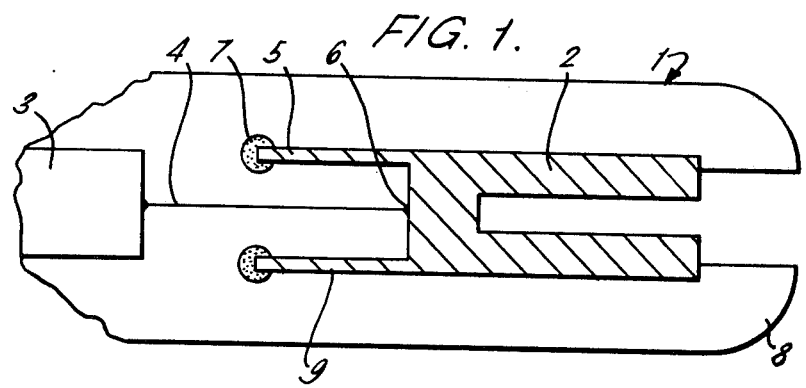
FIG. 1 is a longitudinal section of an embodiment of the invention.

Referring to FIG. 1, a heart pacemaker 1 has an output connector 2 connected to a pulser unit 3 by an output lead 4. The output connector 2 has a shroud portion 5 which extends axially along the output lead 4 so as to cover the junction 6 between the output connector 2 and the output lead 4. A sealing member 7 consisting of a silicone rubber O ring is bended to the free end of the shroud portion 5 of the output connector 2. The whole device is encapsulated in an epoxy resin coating 8.

When the heart pacemaker 1 is assembled, the sealing member 7 is bonded to the shroud portion 5 of the output connector 2, the junction 6 between the output lead 4 and the output connector 2 is made, and the epoxy resin coating 8 is cast. As it cures the epoxy resin coating 8 shrinks, thus compressing the sealing member 7 between itself and the outer surface 9 of the output connector 2 so to prevent the migration of saline body fluids along the surfaces of the shroud portion 5 and thence to the junction 6 between the output connector 2 and the output lead 4.

In use, after implantation, the epoxy resin coating 8 absorbs water from the body tissues of the user of the pacemaker and expands. The pressure on the outer surface of the sealing member 7 is relieved, but due to the expansion of the expoxy resin coating 8 within the shroud member 5, the inward facing surface of the sealing member 7 is now subjected to an increase in pressure thus maintaining the integrity of the seal against the migration of saline body fluids along the surfaces of the shroud portion 5 to the junction 6 between the output connector 2 and the output lead 4.

Figure 2:
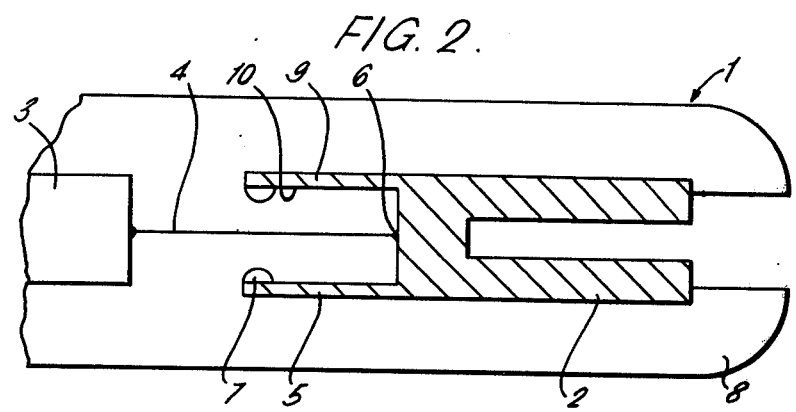
FIG. 2 is a longitudinal section of another embodiment of the invention.

In another embodiment of the invention which is illustrated in FIG. 2, the sealing member 7 is bonded to the inner surface 10 of the shroud portion 5 just inside its free ends. As the epoxy resin coating 8 shrinks on curing, it tends to deform the shroud portion 5, inwardly. This places an initial compressive stress on the sealing member 7, ensuring that it is in intimate contact with the surface of the portion of the epoxy resin coating which is within the shroud portion 5 of the output connector 2, so isolating the junction 6 between the output connector 2 and the output lead 4 from saline body fluids. In use, the expansion of the same portion of the epoxy resin coating 8 maintains the compressive stress in the sealing member 7, thus ensuring that the seal is maintained.

Figure 3:
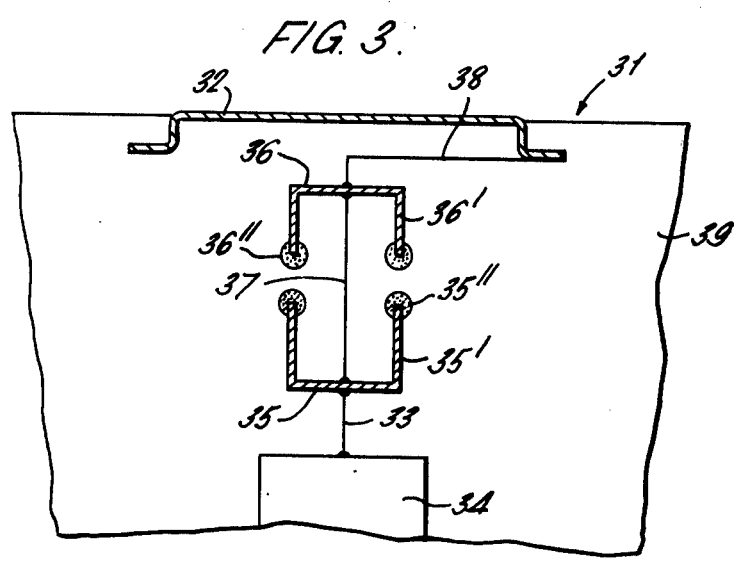
FIG. 3 is a longitudinal section of a third embodiment of the invention.

In another form of heart pacemaker, electrical connection to the patient is made via a larger planar electrode, known as an indifferent plate. Usually the indifferent plate is made of a noble metal such as platinum. Conventionally the remaining metal components of the pacemaker are made of stainless steel. Hence there is a risk of galvanic corrosion, with the stainless steel as the sacrificial material, at the junction between the output lead and the indifferent plate. FIG. 3 illustrates an embodiment of the invention which seeks to combat this problem.

Referring to FIG. 3, a heart pacemaker device 31 incorporated a large platinum planar electrode, or indifferent plate 32 through which electrical pulses produced by the heart pacemaker device 31 are applied to a user of the device. A stainless steel output lead 33 from a pulser unit 34 is connected to a stainless steel first output connector component 35. The first output connector component 35 is connected to a similarly shaped second output component connector 36 by a wire 37. The second output connector component 36 and the wire 37 are both made of platinum. The output connector component 36 is connected to the indifferent plate 32 by a platinum wire 38. Both the first and second output connector component 35 and 36 incorporate shroud portions 35' and 36', respectively, which encompass the reactive junctions with the wire 37. The shroud portions 35' and 36' of connector components 35 and 36 are equipped with annular sealing members 35" and 36", respectively, which function in the same manner as the sealing member 7 in the embodiment of the invention described with reference to FIG. 1. The whole device, with the exception of the outer surface of the indifferent plate 32, is encapsulated in an epoxy resin coating 39.

I claim:

1. A heart pacemaker device including a pulser unit, an output connector and an output lead connecting the pulser unit to the output connector, the whole being encapsulated in a biologically inert material, wherein the output connector incorporates an axially extending shroud portion covering the junction between the output lead and the output connector and there is provided an annular deformable sealing member at the free end of the shroud portion in intimate contact with the shroud portion so as to prevent a body fluid migrating along the surface of the shroud portion of the output connector from gaining access to the junction between the output lead and the output connector.

2. A heart pacemaker according to claim 1 including means for subjecting the sealing member to a compressive stress thereby to establish the intimate contact between the sealing member and the shroud portion of the output connector.

3. A heart pacemaker according to claim 2 wherein the means for subjecting the sealing member to a compressive stress comprises the encapsulating material, said material being of a type which contracts during a curing stage in manufacture thereby to establish the said compressive stress.

4. A heart pacemaker according to claim 1 wherein the encapsulating material comprises an epoxy resin.

5. A heart pacemaker according to claim 1 wherein the sealing member is positioned in contact with the inner surface of the shroud portion of the output connector.

6. A heart pacemaker according to claim 1 wherein the output connector has two components, one connected to the pulser unit of the heart pacemaker and the other connected to a planar output electrode, and each component of the output connector has an axially shroud portion covering the junction between it and the output lead, the shroud portion extending towards each other.

7. A heart pacemaker according to claim 6 including means for subjecting the sealing member associated with each shroud portion to a compressive stress threby to establish the intimate contact between the sealing member and the respective shroud portion of the output connector.

8. A heart pacemaker according to claim 8 wherein the means for subjecting the sealing member to a compressive stress comprises the encapsulating material, the said material being of a type which contracts during a curing stage in manufacture thereby to establish the said compressive stress.

9. A heart pacemaker according to claim 6 wherein each sealing member encloses the free end of the respective shroud portion of the output connector.

* * * * *